United States Patent [19]

Lacaille et al.

[11] Patent Number: 4,948,562
[45] Date of Patent: Aug. 14, 1990

[54] DEVICE FOR DETERMINING A BLOOD GROUP

[76] Inventors: Yves M. Lacaille, 12, avenue Duvelleroy, Nogent sur Marne, France, 94130; Joelle Debear, 19, rue Vignon, Paris, France, 75009

[21] Appl. No.: 310,012

[22] Filed: Feb. 14, 1989

Related U.S. Application Data

[63] Continuation of Ser. No. 52,050, filed as PCT FR86/00297 on Sep. 3, 1986, published as WO87/01461 on Mar. 12, 1987, abandoned.

[30] Foreign Application Priority Data

Sep. 4, 1985 [FR] France .................................. 85 13140
May 27, 1986 [BE] Belgium ................................ 6/48228

[51] Int. Cl.$^5$ ............................................ G01N 33/16
[52] U.S. Cl. ........................................ 422/73; 128/762
[58] Field of Search ...................... 422/61.73, 102; 436/63–69; 128/762–770; 604/415

[56] References Cited

U.S. PATENT DOCUMENTS

| 3,449,081 | 6/1969 | Hughes | 422/61 |
| 3,545,934 | 12/1970 | Dryden et al. | 422/61 |
| 3,554,705 | 1/1971 | Johnston et al. | 422/61 |
| 3,579,306 | 5/1971 | Crane | 422/61 |
| 3,582,283 | 6/1971 | Mirasol, Jr. | 422/61 |
| 3,582,285 | 6/1971 | Hamilton | 422/61 |

FOREIGN PATENT DOCUMENTS 0054087 6/1982 European Pat. Off. .
0104881 4/1984 European Pat. Off. .

Primary Examiner—Christine M. Nucker
Assistant Examiner—T. J. Wallen
Attorney, Agent, or Firm—Marvin Feldman

[57] ABSTRACT

A device is formed with a closed chamber which contains a test serum, and which chamber permits the insertion of a blood sample to be tested. The blood sample and test serum react within the chamber, and the device includes optical elements, such as a magnifying lens, so as to view reaction test results. The test serum may be in a liquid or dry form.

17 Claims, 4 Drawing Sheets

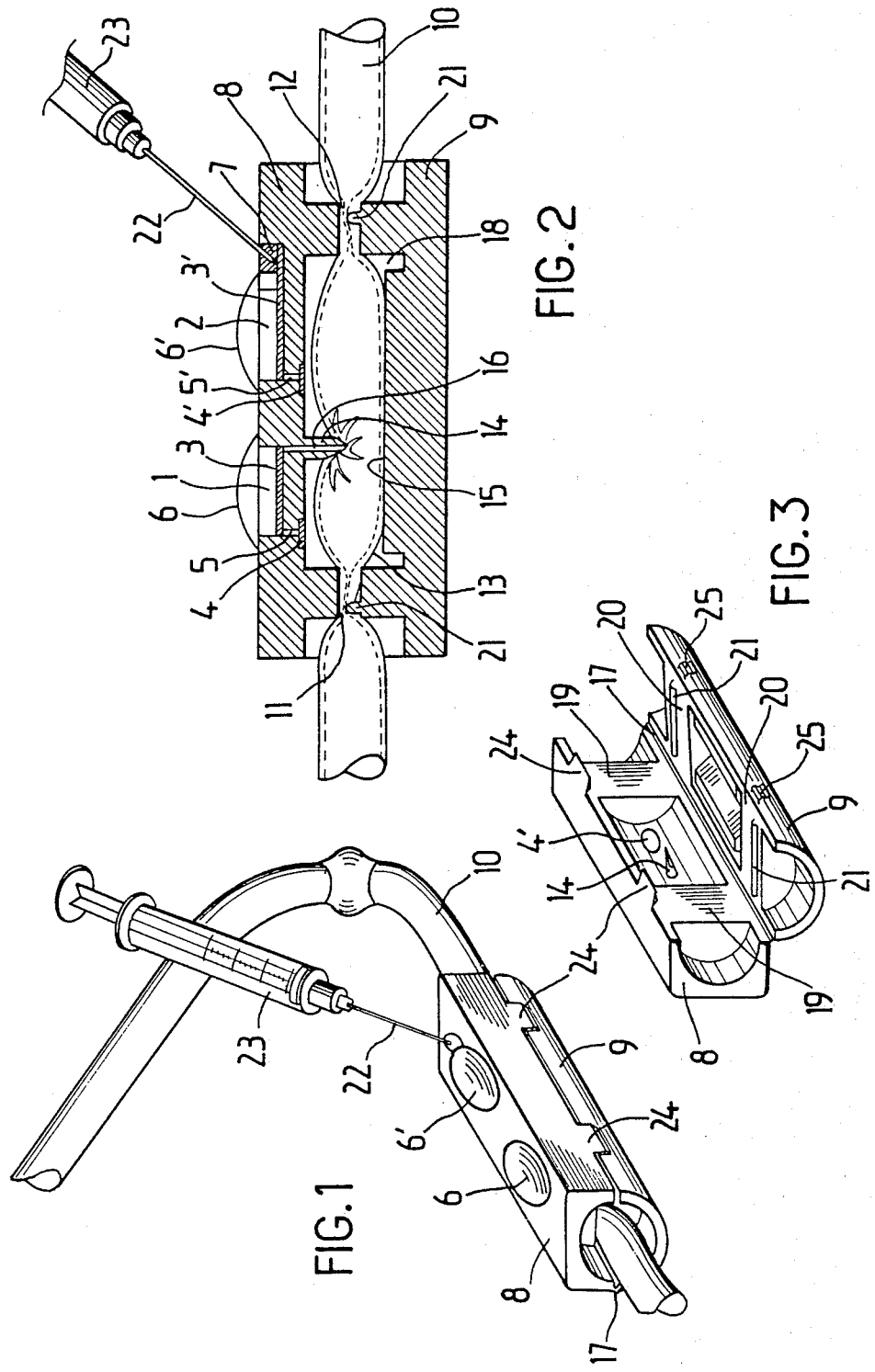

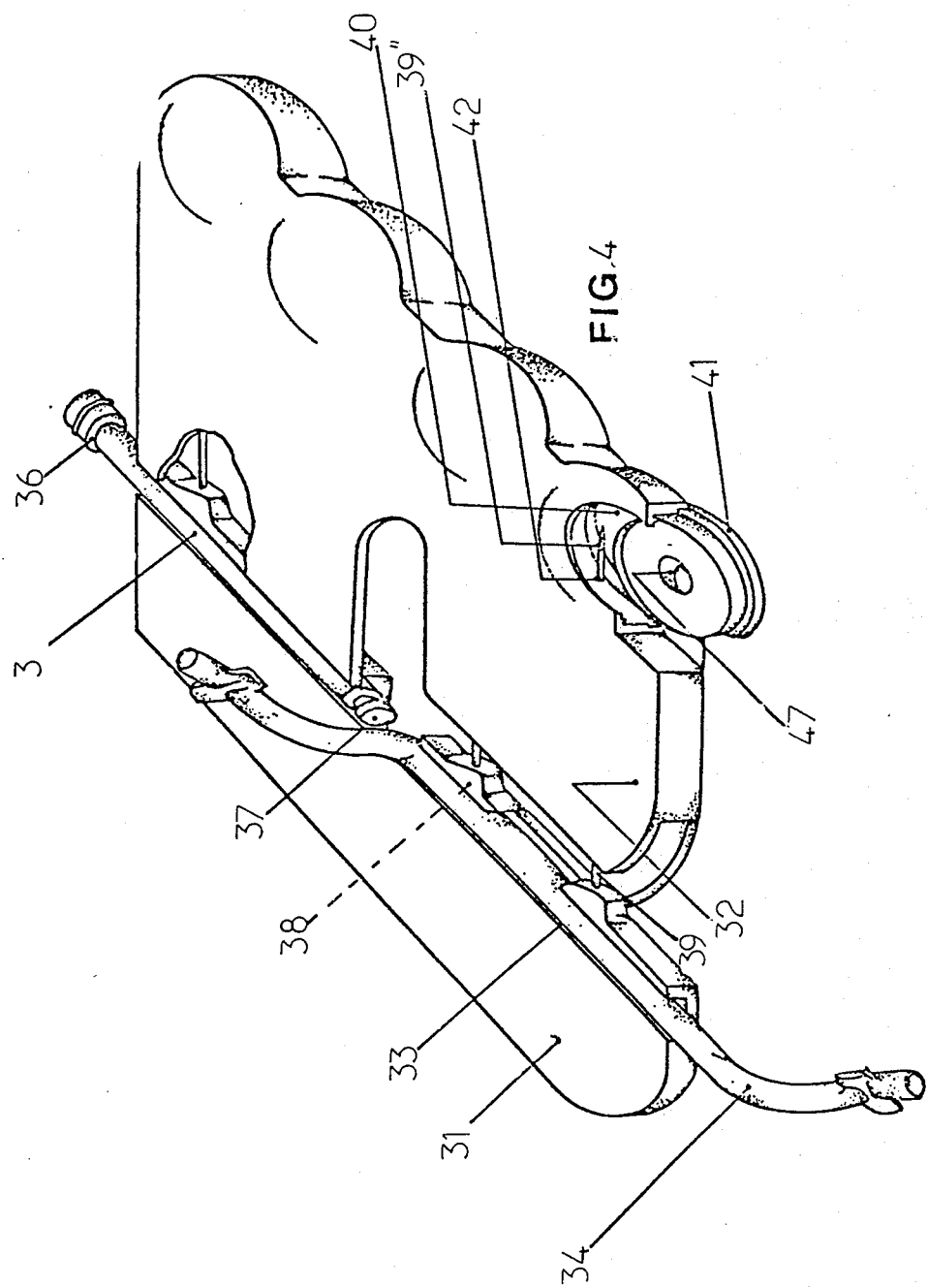

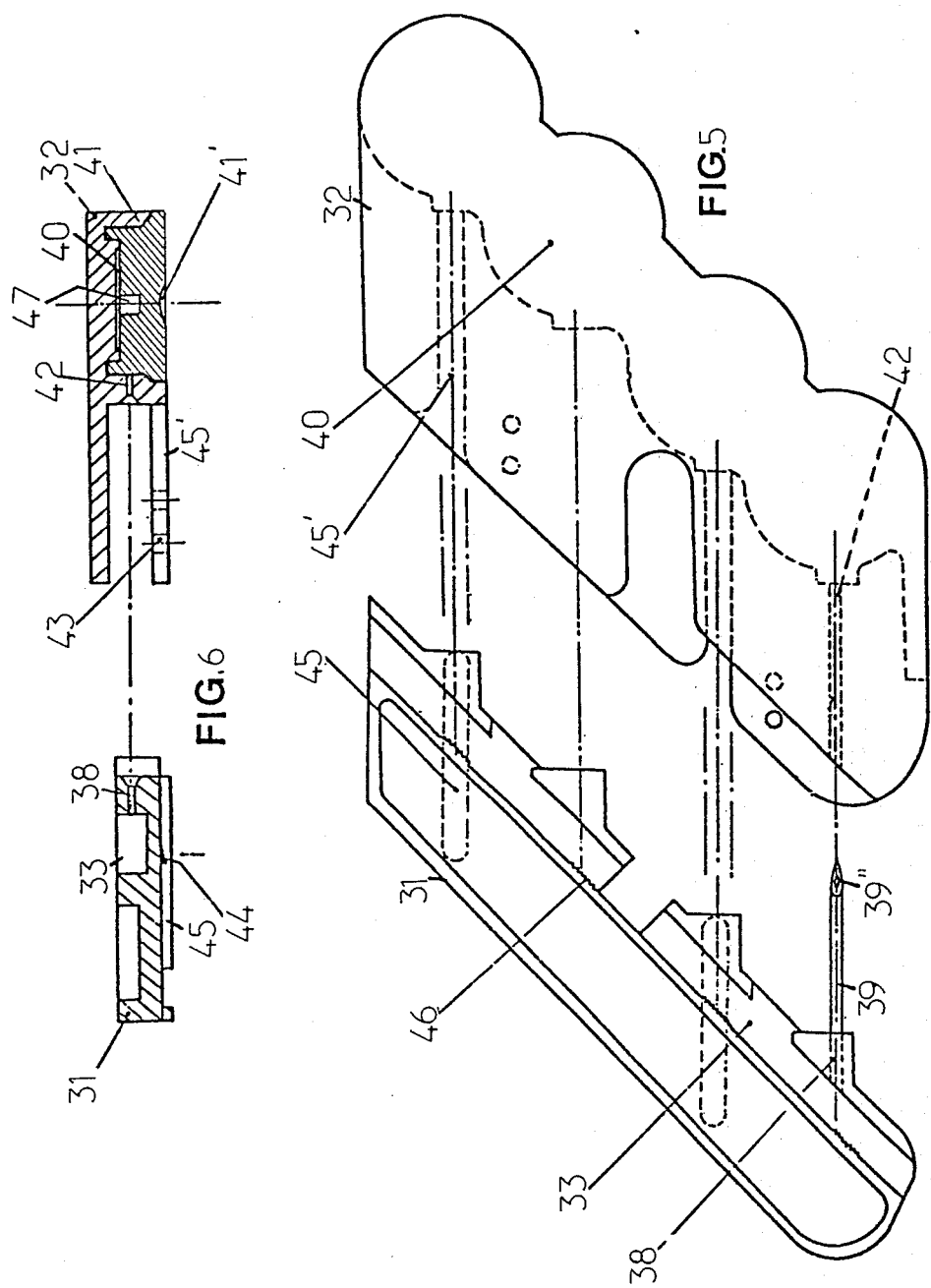

DEVICE FOR DETERMINING A BLOOD GROUP

This is a continuation of co-pending application Ser. No. 052,050 filed as PCT FR86/00297 on Sep. 3, 1986, published as WO87/01461 on Mar. 12, 1987 now abandoned.

The invention relates to a device for determining a blood group, in particular when performing a transfusion.

It is prudent, before performing a blood transfusion, to verify that the blood which is about to be transfused does not have any incompatibilities with the blood of the recipient, with such incompatibilities arising, for example, from an error in labelling or an error in transcribing the blood group of the recipient.

In particular, in some countries including France, regulations require that such verification should be performed at least with respect to groups A/B/0, since incompatibility in this respect gives rise to very serious consequences very soon after transfusion begins.

Blood groups are usually determined by placing a drop of the blood to be indentified and a drop of test serum on a plate, with the appearance of the resulting mixture indicating the group. A variant of this method consists in using a test serum which has been crystallized onto a card medium. The test serum is then diluted using water at the moment of use and the blood to be tested is added thereto.

These methods require awkward manipulations which also include risks of contamination for the manipulator since they take place in free air and thus under conditions of doubtful asepsis.

The invention seeks to simplify the implementation of the verifications which are necessary before a blood transfusion.

Another aim is to enable said implementation to take place under improved conditions of hygiene.

Yet another aim is to make it easy to keep the result of the test fixed to the bag of blood which has been tested.

The invention provides a device for determining a blood group, the device being characterized in that it comprises at least one closed chamber, means for inserting a sample of blood to be tested into said chamber in order to put it into contact with a test serum, and means for enabling the reaction of the test serum with the blood to be observed.

Means may also be provided for inserting the test serum into the chamber.

In a variant, the test serum may be present in the chamber in advance, either in the liquid state or in the dry state, e.g. in the form of crystals, or else impregnating a porous medium.

In one embodiment of the invention, the chamber is closed in gas-tight manner and is placed under a vacuum before the blood is inserted therein, and the means for inserting the blood include a moving member suitable for putting the inside of the chamber into communication with a receptacle containing the blood to be identified, thereby enabling a sample of said blood to be sucked into the chamber.

This ensures that the quantity of blood transferred into the chamber is determined by the degree of vacuum, i.e. by the residual pressure in the chamber at the moment when it is put into communication with the receptacle.

According to a characteristic of the invention, the moving member is hollow needle which perforates a wall of the chamber. This needle may have points at both ends for respectively and successively perforating the wall of the receptacle and the wall of the chamber.

In a particular embodiment of the invention, the device comprises a housing made of two parts each displaceable relative to the other and each displacable relative to the needle, with the chamber and the receptacle being contained in respective ones of said two parts and with the relative motion of said parts causing the wall of the receptacle and the wall of the chamber to be perforated successively by the points of the needle.

Advantageously, the relative displacement of the two parts of the housing is a sliding displacement and the needle is guided in channels provided in the two parts and aligned in the direction of sliding.

In a implementation of the invention, the perforatable wall of the chamber is defined by a plug which co-operates with one of the parts of the housing to constitute the sealed chamber.

The plug may be pressed into a recess in the part in order to close it in sealed manner.

When at least two chambers are provided, each intended for identifying a respective one of two blood samples by means of the same test serum, the two chambers may be juxtaposed along the length of a flexible hose received in a hollow in the second part and constituting the receptacle for the corresponding blood sample, with the relative displacement of the two parts taking place transversely to said direction.

In the device comprising four chambers for identifying two different blood samples by means of two different test serums, it is advantageous to house two hoses in alignment with each other in an elongate hollow, with the hoses respectively containing the two blood samples to be identified and with the four chambers being aligned along the hose direction.

Other characteristics and advantages of the invention appear from the detailed description given below and from the accompanying drawings, in which:

BRIEF DESCRIPTION OF THE DRAWINGS

FIG. 1 is a perspective view showing a device in accordance with the invention closed over a flexible hose containing blood, together with a syringe for injecting a sample of blood therein;

FIG. 2 is a longitudinal section through the device shown in FIG. 1;

FIG. 3 is a perspective view showing the device on its own and open;

FIG. 4 is a perspective view of a second device in accordance with the invention showing two slidable portions partially interfitted;

FIG. 5 is a plan view of the FIG. 4 device with the two slidable portions being dissociated;

FIG. 6 is a cross-section corresponding to FIG. 5; and

DETAILED DESCRPITION OF THE DRAWINGS

Figure 7:
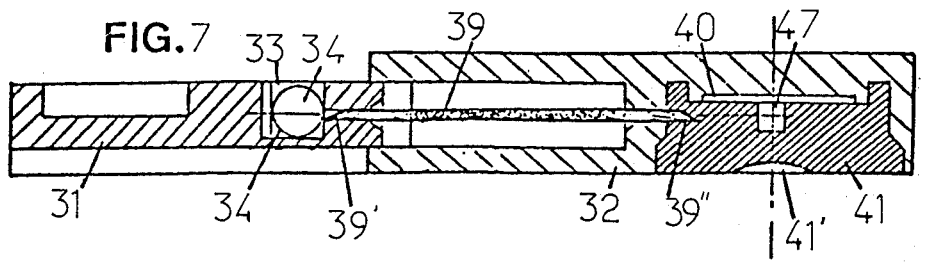
FIGS. 7 to 10 are section views showing four stages in moving needle displacement.
Figure 8:
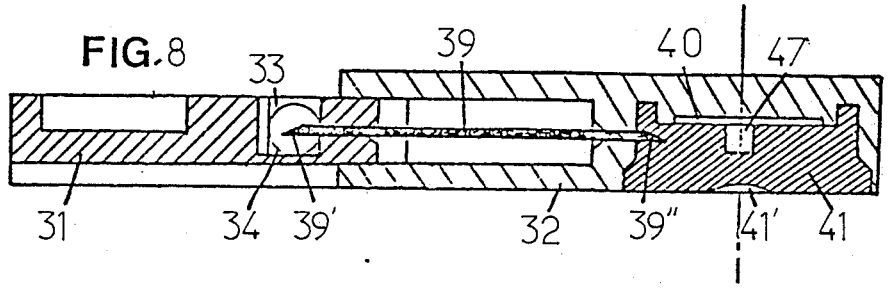

The device shown in FIGS. 1 to 3 comprises two portions 8 and 9 which are connected by the hinge 17 enabling them to be closed against each other. When they are closed together in this way, the portions 8 and 9 define a housing 18 therebetween for an intermediate portion 13 of a flexible hose 10, said intermediate portion lying between two zones 11 and 12 which are clamped between facing faces 19 and 20. Ribs 21 projecting from the face 20 of the portion 9 co-operate with the face 19 of the portion 8 to close off the portion 13 in substantially leak-proof manner from the remainder of the hose 10.

A needle 14 fixed to the protion 8 of the device projects into the housing 18. This needle has a duct 16 running there-along right up to its end where it opens out into the housing 18, thereby connecting the housing with a closed chamber 1 provided in the portion 8. The chamber 1 is also connected to the housing 18 via another duct 5 which is closed by a hydrophobic membrane 5 which is permeable to the air. The chamber 1 contains a porous medium 3 impregnated with a test serum in the dry state. The chamber 1 is separated from the outside of the device by a magnifying lens 6.

Another chamber 2 is provided in the portion 8, likewise associated with a medium 3' impregnated with test serum, a duct 5' having a hydrophobic membrane 4', and a magnifying lens 6' similar to the items described under reference numerals 3 to 6 with reference to the chamber 1. Adjacent to the chamber 2 there is an element 7 which is capable of being perforated by a needle and which is accessible from the outside of the device.

The device operates as follows:

On being opened, the device is put into position shown in FIG. 3 enabling the flexible hose 10 connected to a supply of blood to be transfused and filled with said blood to be put into place between the portions 8 and 9 running parallel to the hinge 17. Once the hose has been put into place, the two portions 8 and 9 of the device are closed over the hose as shown in FIGS. 1 and 2. Co-operation between the ribs 21 and the surfaces 19 then isolates a volume of blood in the intermediate portion 13 of the hose. This intermediate portion presses against the surface 15 of the portion 9 delimiting the housing 18 and facing the needle 14, thereby ensuring that said needle is certain to perforate the wall of the intermediate portion 13 of the hose while the device is being closed.

Under the effect of the pressure inside the portion 13 blood flows from said portion into the chamber 1, with said pressure being increased by the volume reduction due to the zones 11 and 12 of the hose 10 being pressed together over a certain length between the surfaces 19 and 20 of the portions 8 and 9. The empty space in the chamber 1 is filled with blood while the air originally contained therein escapes via the duct 5 and the membrane 4, with the membrane 4 preventing the blood from flowing out from the chamber.

The blood reacts with the test serum 3 and the results may be observed through the magnifying lens 6.

Further, the plug 7 is perforated by means of a needle 22 mounted on a syringe 23 and containing the recipient's blood thereby injecting said blood into the chamber 2. Air escapes from the chamber 2 and the reaction is observed in the manner described with reference to the chamber 1.

Locking tabs 24 on the portion 8 co-operate with notches 25 on the portion 9 and hold the device in its closed position.

After observing that the same reaction has taken place in both chambers 1 and 2, it is possible to proceed with the transfusion. If so desired, the device may be left in place on the hose 10, with the needle 14 remaining engaged in the hose wall. This makes it possible at any moment while transfusion is taking place to verify that the test has indeed been performed and to check the results thereof.

The device described above identifies blood by means of a single test serum. In order to verify blood compatibility with respect to the groups A/B/0, it is necessary to use two test serums, anti-A and anti-B, so two devices can be used, one for each test serum.

Another solution consists in using modified device including four chambers, i.e. a pair of chambers similar to the chamber 1 for the blood to be transfused and a pair of chambers similar to chamber 2 for the recipient's blood, with one chamber in each pair containing anti-A test serum and the other containing anti-B test serum. The relative positions of these four chambers depends on a design choice of the preson skilled in the art. For example, they may be placed in one or two lines behind a single face of the device or in pairs behind two adjacent faces thereof. Another design choice for the person skilled in the art concerns whether the two chambers for receiving the blood to be transfused are to be supplied via a single needle, via a branch in the duct thereof, or via two separate needles.

The invention also covers a device including only one or two chambers for receiving blood to be transfused, and usable, in particular, for testing successive units of blood to be transfused to the same recipient whose own blood has already been tested while testing the first unit.

The invention also covers a device comprising one, two, or four chambers or even more provided with an element such as 7 capable of being perforated by a needle and not including a built-in needle. Such a device having one or more chambers may be used for testing a single blood sample by means of one or more test serums, for expamle a blood sample taken from a person independently of any transfusion operation. With a suitable number of chambers, this makes it possible, in particular, to perform a complete blood group test of the kind performed in a laboratory. A device including an even number of chambers may be used for checking compatibility prior to transfusion when the supply of blood to be transfused is not connected to a flexible hose capable of being clamped and perforated, for example when the supply is in a glass bottle associated with a small test bottle.

It is also possible to provide single chamber devices and to use an appropriate number of them as a function of the tests to be performed by putting them into place, where appropriate, individually along a flexible hose associated with a supply of blood.

Whenever such a flexible hose is not available, the device may be simplified by omitting the hinge and the bearing surface. For use in conjunction with a flexible hose, the two hinged portions may be replaced by two separate portions provided with assembly means. e.g. by inter-fitting.

Further, the needle 14 for perforating the hose may be replaced by a blade for cutting it.

The various versions of the device in accordance with the invention may be stored in sterile packaging until they are used, thereby making it possible to perform blood tests under sterile conditions.

The porous media 3 impregnated with test serum may be replaced by test serum in the liquid state, or in the crystal state without a supporting medium. In this case, the duct 16 must be narrow enough to prevent the crystals from escaping. If the serum is liquid, a non-return valve type of sealing device may be provided, e.g. in the form of a small ball. When the test serum is in the dry state, it may be advantageous to provide water in the chamber in order to dilute it in use, and this water may be contained in one or more frangible receptacles which are broken, e.g. by pressing against the lenses 6 made of flexible plastic material.

It is also possible to omit inserting the test serum or the dilution water in the chambers in advance and then, when a test is to be performed, to inject them via elements such as 7 which need to be associated with each of the chambers, or to insert them by opening the chambers, e.g. by means of one or more covers provided for the purpose.

The device shown in FIGS. 4 to 10 comprises two housing parts or portions 31 and 32 which are slidable relative to each other. The upper portion 31 has a groove 33 for receiving both a hose 34 coming from a bag of blood (not shown) and a test hose 35 for receiving a sample of blood from the recipient.

The test hose 35 includes a plug 36 which can be perforated by a needle in order to insert the sample of the recipient's blood and a permeable plug 37 for allowing air to escape. The upper portion also includes channels 38 for guiding moving needles 39.

The lower portion 32 includes a set of chambers 40 each of which is closed by means of plug 41 and each of which is provided with a channel 42 in which a corresponding moving blood-inserting needle 39 can slide.

The hollow moving needles 39 are placed during manufacture in the channels 42 and 38 of the lower and upper portions 32 and 31, and each end of each needle has a respective chamfer 39' or 39".

In the embodiment shown, the device includes a set of chambers which are mutually separated from one another, and it preferably includes an even number of chambers so as to be able to test stored blood and the blood of the recipient simultaneously. Advantageously, the device includes four chambers with one pair of the donor's blood and one pair for the recipient's blood.

The axis of the groove 33 in the upper portion 31 and the axes of the guide channels 38, 42 for needles 39 intersect at an angle lying in the range 30° to 60°. This slope of the needle guide channels is to enable them to penetrate firstly into the test hoses 34 and 35 at a favorable angle that reduces the penetration force and also improves sealing at the location where penetration occurs.

The device described above operates as follows:

The chambers 40 are initially checked to verify that they are still under reduced pressure by examining the plugs 41 which should have a small central dip 40', with the pressure reduction in the chambers being obtained by any conventional means, for example by placing the device in a vacuum chamber at an appropriate moment during manufacture.

The sample of recipient's blood is injected into the test hose 35 provided for the purpose.

The test hose 34 from the blood bag is inserted into the groove 33 provided for the purpose and the upper portion 31 is pressed to a first ridge 43 to which it is locked by a catch 44.

The application of a small amount of pressure causes the upper portion 31 to slide in the lower portion 32 until it comes into abutment (FIG. 8) with the two parts being guided relative to each other by means of slideways 45 and 45'.

Figure 9:
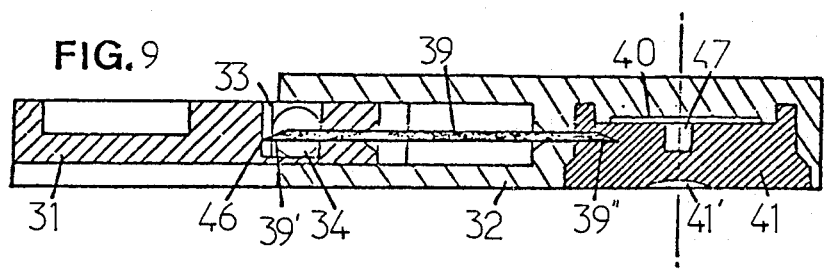

The moving needles 9 begin by perforating the test hoses 34 and 35 containing the blood to be tested and pass right through them until their chamfered tips 39' come into abutment against the bottom of the groove 33. The chamfer angle and its orientation are chosen so that the tips of the needles 39 are received in serrated portions 46 provided for this purpose in the upper portion 31 without establishing communication between the blood contained in the hose and the outside of the device (FIG. 9).

Figure 10:
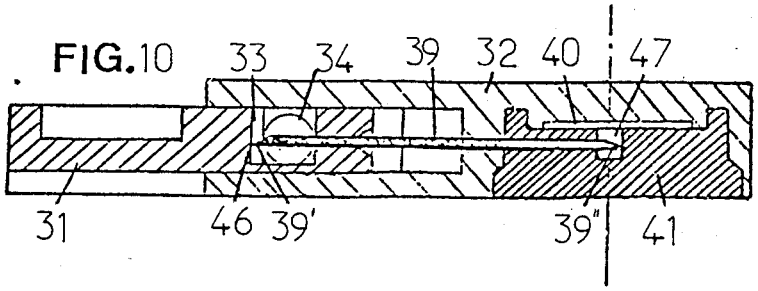

Thereafter, under the effect of relative displacement between the two portions 31 and 32, the needles 39 pass through the thickness of the wall of the plugs 31 until they open out into the cavities 47 provided therein at reduced pressure. Under the effect of this reduced pressure, a calibrated volume of blood is sucked into each chamber 40 and is intimately mixed with serum previously placed therein (FIG. 10).

The samples are inspected visually through the top walls of the chambers since the device is made of transparent material.

During manufacture, test serum is inserted in the, or each, chamber 40 and preferably in the liquid state. Once the test serum has been inserted in a chamber, it is put under reduced pressure and closed by a plug 41.

The chambers are shaped so that serum and blood mix in a uniform manner to provide a smooth thin film as can be seen from the FIG. 7 section through a chamber. This facilitates agglutination and makes it easier to perform visual comparison between chambers.

The pressure reduction inside the chamber is adjusted so as to suck in a constant volume of blood and it is accurately matched to the volume of serum placed in the chamber so as to obtain an ideal mixture for agglutination and interpretation.

By virtue of the catches 44 and the ridges 43, the device is provided with a system for locking the two portions together so that they cannot be moved apart after they have been used. Once the two portions 31 and 32 have been locked together, the device remains fixed to the test hose 34 of the blood bag, thereby avoiding possible confusion.

At no moment during the various stages are the test hoses 34 and 35 subjected to pressure and there is therefore no danger of blood seeping out from the device.

As with the device shown in FIGS. 1 to 3, the device shown in FIGS. 4 to 10 may include various different numbers of chambers depending on its purpose. Similarly, each chamber may contain no test serum or may contain a a test serum which is liquid or dry.

We claim:

1. A device for determining a blood group, including:
   a first body member comprising a closed reaction chamber for containing a test serum,
   a second body member,
   reservoir means for containing a sample of blood to be tested,
   means associated with said first and second body members for maintaining same and said reservoir means joined together while allowing displacement of the first body member relative to the second body member and to the reservoir means between an open position and a closed position of the device,
   means for establishing a pressure difference between said chamber and said reservoir means, with the pressure in the latter being higher than the pressure in the chamber, and,
   an element being formed with a hollow portion disposed between said reservoir means and said reaction chamber, means displaceable relative to said reservoir means as a result of the displacement of said first body member towards said closed position for piercing said reservoir means and establishing a path through said hollow element between said reservoir means and said reaction chamber for directly transferring a predetermined amount of blood from the reservoir means to the reaction chamber, due to said pressure difference, thereby allowing said amount of blood to form a reaction with said test serum in said chamber, and wherein said first body member includes means for visually observing a result of said reaction.

2. A device according to claim 1, further including means for inserting the test serum into the chamber.

3. A device according to claim 1, wherein the test serum is disposed in the chamber.

4. A device according to claim 3, wherein the test serum is present in the liquid state.

5. A device according to claim 3, wherein the test serum is present in the dry state.

6. A device according to claim 1, including at least one pair of reaction chambers including two different respective test serums.

7. A device according to claim 1, including a pair of reaction chambers for containing the same test serum, the chambers of said pair being intended for identifying respectively blood from a patient who is to receive a transfusion and the blood intended for said transfusion.

8. A device according the claim 1, including two pairs of reaction chambers, the chambers of one of said pairs being intended for containing a test serum different from the one contained in the chambers of the other pair, and the chambers of each pair being intended for identifying respectively blood from a patient who is to receive a transfusion and the blood intended for said transfusion.

9. A device according to claim 1, wherein the reaction chamber is closed in a gas-tight manner and is evacuated prior to blood being inserted therein.

10. A device according to claim 1, wherein the hollow element has points at both ends which respectively perforate a wall of the reservoir means and a wall of the chamber.

11. A device according to claim 10, wherein the hollow element is movable relative to both body members, said reservoir means being located in said second body member.

12. A device according to claim 11, at least one of said body members being slidable, wherein said relative movement is a sliding movment, and the hollow element is guided in channels of the body members which are aligned in the sliding direction.

13. A device according to claim 11, wherein said wall of the chamber is defined by a plug which co-operates with the first body member to constitute the gas-tight chamber.

14. A device according to claim 13, said first body member being formed with a recess, wherein the plug is pressed into a recess of the first body member for closing said recess in a gas-tight manner.

15. A device according to claim 11, wherein the reservoir means includes a hose received in the second body member.

16. A device according to claim 15, at least one of said body members being slidable relative to the other, including at least one pair of reaction chambers for idenifying the blood contained in such reservoir means, the chambers of one pair being aligned with the hose, which is transverse to the directon of said sliding.

17. A device according to claim 16, including two pairs of reaction chambers having two hoses for identifying respectively two different bloods contained in respective hoses with the four chambers being aligned with said hoses.

* * * * *